United States Patent
Lee et al.

(10) Patent No.: US 11,337,464 B2
(45) Date of Patent: May 24, 2022

(54) SYSTEM FOR CHARGING AEROSOL GENERATION DEVICE

(71) Applicant: KT&G CORPORATION, Daejeon (KR)

(72) Inventors: Jong Sub Lee, Seongnam-si (KR); In Seong Chun, Goyang-si (KR)

(73) Assignee: KT&G CORPORATION, Daejeon (KR)

( * ) Notice: Subject to any disclaimer, the term of this patent is extended or adjusted under 35 U.S.C. 154(b) by 214 days.

(21) Appl. No.: 16/617,200

(22) PCT Filed: May 24, 2018

(86) PCT No.: PCT/KR2018/005894
§ 371 (c)(1),
(2) Date: Nov. 26, 2019

(87) PCT Pub. No.: WO2018/217030
PCT Pub. Date: Nov. 29, 2018

(65) Prior Publication Data
US 2021/0127757 A1 May 6, 2021

(30) Foreign Application Priority Data

May 26, 2017 (KR) ......................... 10-2017-0065543
May 26, 2017 (KR) ......................... 10-2017-0065544
(Continued)

(51) Int. Cl.
*A24F 13/00* (2006.01)
*A24F 40/95* (2020.01)
(Continued)

(52) U.S. Cl.
CPC .............. *A24F 40/95* (2020.01); *A24F 40/20* (2020.01); *A24F 40/57* (2020.01)

(58) Field of Classification Search
CPC ...................................................... A24F 47/00
(Continued)

(56) References Cited

U.S. PATENT DOCUMENTS 9,220,304 B2    12/2015  Greim
9,247,773 B2     2/2016  Memari et al.
(Continued)

FOREIGN PATENT DOCUMENTS

CN       104105417 A    10/2014
CN       104135880 A    11/2014
(Continued)

OTHER PUBLICATIONS

International Search Report for PCT/KR2018/005894 dated Aug. 29, 2018 [PCT/ISA/210].
(Continued)

*Primary Examiner* — Phuong K Dinh
(74) *Attorney, Agent, or Firm* — Sughrue Mion, PLLC

(57) ABSTRACT

Discloses is a aerosol generating system including: an aerosol generation device configured to generate an aerosol by heating an aerosol generating material; and an external power supply device including a case, a charger receiving unit which is rotatably coupled to the case and configured to receive the aerosol generation device in a detachable manner such that the aerosol generation device is driven in one of a charging mode, a cleaning mode, a preheating mode, and a smoking mode while being received in the charger receiving unit.

14 Claims, 10 Drawing Sheets

(30) Foreign Application Priority Data

May 26, 2017 (KR) .......................... 10-2017-0065545
May 9, 2018 (KR) .......................... 10-2018-0053202

(51) Int. Cl.
*A24F 40/20* (2020.01)
*A24F 40/57* (2020.01)

(58) Field of Classification Search
USPC ................................................ 131/328–329
See application file for complete search history.

(56) References Cited

U.S. PATENT DOCUMENTS

| | | | |
|---|---|---|---|
| 10,548,350 | B2 | 2/2020 | Greim et al. |
| 2015/0020832 | A1 | 1/2015 | Greim et al. |
| 2015/0245654 | A1* | 9/2015 | Memari ............... H02J 7/35 141/2 |
| 2016/0366846 | A1* | 12/2016 | Mcgowen ............. A01H 5/10 |
| 2016/0366946 | A1 | 12/2016 | Murison et al. |
| 2017/0033568 | A1 | 2/2017 | Holzherr |
| 2017/0045150 | A1 | 2/2017 | Marsh |
| 2017/0150758 | A1 | 6/2017 | Fernando et al. |

FOREIGN PATENT DOCUMENTS

| | | |
|---|---|---|
| CN | 106163307 A | 11/2016 |
| JP | 2015-504669 A | 2/2015 |
| KR | 20-0479425 Y1 | 1/2016 |
| KR | 10-1667502 B1 | 10/2016 |
| KR | 10-2016-0129024 A | 11/2016 |
| KR | 10-2016-0142896 A | 12/2016 |
| KR | 10-2016-0147253 A | 12/2016 |
| WO | 2015/128665 A1 | 9/2015 |

OTHER PUBLICATIONS

Written Opinion for PCT/KR2018/005894 dated Aug. 29, 2018 [PCT/ISA/237].
Korean Office Action for 10-2017-0065543 dated May 26, 2017.
Korean Office Action for 10-2017-0065544 dated May 26, 2017.
Korean Office Action for 10-2017-0065545 dated May 26, 2017.
Communication dated Feb. 24, 2021 from the Japanese Patent Office in Application No. 2019-564921.
Extended European Search Report dated Jan. 28, 2021 from the European Patent Office in Application No. 18806149.3.
Office Action dated Oct. 29, 2021 from the China National Intellectual Property Administration in CN Application No. 201880033366.5.

\* cited by examiner

SYSTEM FOR CHARGING AEROSOL GENERATION DEVICE

CROSS-REFERENCE TO RELATED APPLICATIONS

This application is a National Stage of International Application No. PCT/KR2018/005894 filed on May 24, 2018, claiming priority based on Korean Patent Application Nos. 10-2017-0065543 filed on May 26, 2017, 10-2017-0065544 filed on May 26, 2017, 10-2017-0065545 filed on May 26, 2017 and 10-2018-0053202 filed on May 9, 2018.

BACKGROUND

1. Field of the Invention

Exemplary embodiments of the present disclosure relate to a charging system for an aerosol generation device, the charging system having various power supply units.

2. Description of Related Art

Recently, the demand for alternative methods to overcome the shortcomings of general cigarettes has increased. For example, there is an increasing demand for a method of generating aerosol by heating an aerosol-generating material in cigarettes, not a method of generating aerosol by combusting cigarettes. Accordingly, studies on a heating-type cigarette or a heating-type aerosol generation device have been actively conducted.

Puffing of preference substances, such as smoking, may be achieved by puffing aerosol in air, that is, aerosol. In the past, conventional cigarettes were almost the only means of inhaling such preference substances, but recently, electronic cigarettes have become another means. Electronic cigarettes generate aerosol by vaporizing the inhaled substance into vapors by applying heat or ultrasonic waves to a cartridge containing the inhalation substance in liquid form. Accordingly, electronic cigarettes are completely differentiated from the conventional cigarettes that generate smoke by combustion, and thus can prevent the generation of a variety of harmful substances that may occur due to the combustion.

In addition, according to the demands of consumers who prefer a conventional cigarette in the form of a cigarette, an electronic cigarette having a filter portion, as that in the conventional cigarette, and a cigarette portion has also been proposed. The electronic cigarette has such a structure that a user puffs a puffing material through the filter portion having the same configuration as in the conventional cigarette by vaporizing the puffing material included in the cigarette portion by an electric heater. In such an electronic cigarette, unlike the conventional cigarette in which the cigarette portion is filled with dry tobacco leaves, the cigarette portion is impregnated with the puffing material or filled with paper coated with the puffing material. When the electronic cigarette is inserted into a holder and a heater inside the holder is heated to vaporize the puffing material inside the cigarette portion, the user may puff the puffing material vaporized through the filter portion. As such, in addition to maintaining the non-combustion, which is the advantage of conventional electronic cigarettes, such an electronic cigarette allows a user to inhale the vaporized puffing material through the filter portion, which is the same mechanism as when smoking conventional cigarettes. Accordingly, the user may experience the same feeling as smoking conventional cigarettes.

In the case of an electronic cigarette, following a certain period of use, a charger, which has been installed inside therein, is separated from the electronic cigarette and then re-charged by using a separate charging device before use. Conventionally, after one or two days of use, the battery is discharged and needs to be recharged. Accordingly, the electronic cigarette often stops in the middle of user's puffing. A larger capacity of the battery can prolong the use time of the electronic cigarette, but this may result in an increase in the size of the battery and an increase in the weight and size of the electronic cigarette. Although an electronic cigarette with a replaceable battery is available in the market, it may be inconvenient because a user has to carry the battery at all times. Also, it is inconvenient to separate and recharge the battery, which raises a concern about battery loss.

BRIEF SUMMARY OF THE INVENTION

Exemplary embodiments of the present disclosure provide a charging system for an aerosol generation device that does not involve combustion and is capable of diversifying puffing materials.

In addition, Exemplary embodiments of the present disclosure provide a charging system for an aerosol generation device that can be continuously used without interruption in use during user puffs.

In addition, Exemplary embodiments of the present disclosure are to provide a charging system for an aerosol generation device to which electric power is easily supplied and which is portable and easy to use, by means of a detachable power storage device or an additional auxiliary power storage device.

An exemplary embodiment of the present disclosure provides a system for charging an aerosol generation device, the system including: an aerosol generation device including a heater for generating heat by resistance when a current is applied thereto, a power storage unit for supplying electric power to the heater, and a controller for controlling the heater; and an external power supply device including a case, a charger receiving unit mounted rotatably on the case and receiving the aerosol generation device in a detachable and attachable manner, an auxiliary power storage device for storing the power to be delivered to the aerosol generation device, and an auxiliary power supplying device for controlling the auxiliary power storage device to supply electric power to the aerosol generation device, wherein the aerosol generation device is driven in one mode of a charging mode, a cleaning mode, a preheating mode, and a smoking mode, according to where the aerosol generation device is received in the charger receiving unit.

Exemplary embodiments of the present disclosure provide a charging system for an aerosol generation device capable of vaporizing an aerosol-forming material without involving combustion.

In addition, provided is a charging system for an aerosol generation device that is powered in a variety of ways to prevent unwanted stop of operation.

DETAILED DESCRIPTION OF THE INVENTION

Figure 1:
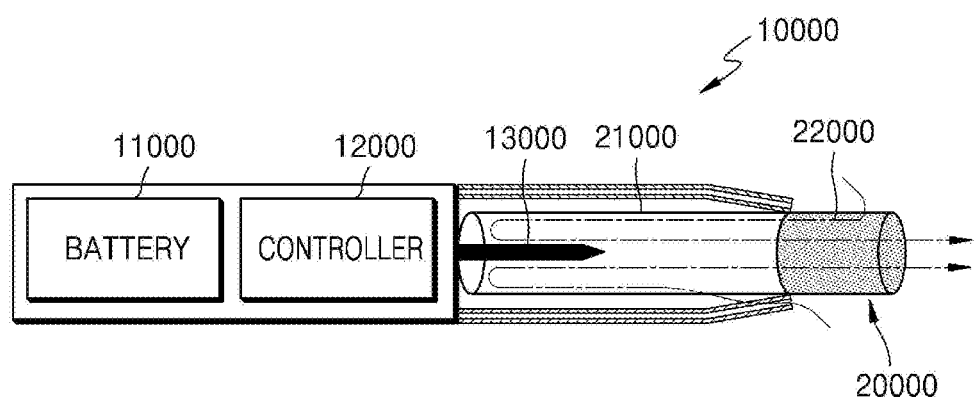
FIG. 1 is a schematic view illustrating an exemplary embodiment in which a cigarette is inserted into an aerosol generation device.

An exemplary embodiment of the present disclosure provides a system for charging an aerosol generation device, the system including: an aerosol generation device including a heater for generating heat by resistance when a current is applied thereto, a power storage unit for supplying electric power to the heater, and a controller for controlling the heater; and an external power supply device including a case, a charger receiving unit mounted rotatably on the case and receiving the aerosol generation device in a detachable and attachable manner, an auxiliary power storage device for storing the power to be delivered to the aerosol generation device, and an auxiliary power supplying device for controlling the auxiliary power storage device to supply electric power to the aerosol generation device, wherein the aerosol generation device is driven in one mode of a charging mode, a cleaning mode, a preheating mode, and a smoking mode, according to where the aerosol generation device is received in the charger receiving unit.

In one embodiment, the charger receiving unit may have facing side surfaces which have holes passing through the charger receiving unit, grooves are formed in positions corresponding to the holes inside the case, the charger receiving unit is coupled to the case by means of a hinge inserted into the holes and the grooves simultaneously through the holes and the grooves, and the charger receiving unit is rotatable about the hinge with respect to the case.

In one embodiment, the charger receiving unit includes a first charging terminal which is electrically connected to the auxiliary power storage device and the auxiliary power supplying device and is exposed to the outside, and the aerosol generation device, when mounted on the charger receiving unit, further includes a second charging terminal connected to the first charging terminal.

In one embodiment, the auxiliary power supplying device may supply electric power for charging or cleaning or electric power for preheating or smoking to the aerosol generation device received in the charger receiving unit through the first charging terminal.

In one embodiment, the charger receiving unit may be rotatable between a first position where the charger receiving unit is positioned parallel to a longitudinal direction of the case, and a second position where the charger receiving unit is positioned crossing the longitudinal direction of the case.

In one embodiment, the external power supply device may further include a first magnetic body and a second magnetic body provided on the case, wherein the first magnetic body and the second magnetic body face each other about the rotation center of the charger receiving unit, and the charger receiving unit may include a third magnetic body facing one of the first magnetic body and the second magnetic body.

In one embodiment, the charger receiving unit may maintain the first position by an attraction force between the third magnetic body and one of the first magnetic body and the second magnetic body.

In one embodiment, the aerosol generation device may further include a fourth magnetic body facing the other one of the first magnetic body and the second magnetic body.

In one embodiment, the charger receiving unit may maintain the second position by an attraction force between the fourth magnetic body and the other one of the first magnetic body and the second magnetic body.

In one embodiment, the power storage unit may be provided in a cylindrical shape inside the aerosol generation device, and the fourth magnetic body may surround a portion of an outer portion of the power storage unit.

In one embodiment, the charger receiving unit may be configured to have a round internal surface to correspond to an outer surface of the aerosol generation device and receive the aerosol generation device, and when the aerosol generation device is received in the charger receiving unit, the aerosol generation device is aligned inside the charger receiving unit in such a manner that the distance between a centerline of the fourth magnetic body and the second magnetic body is the shortest.

In one embodiment, the first magnetic body and the second magnetic body may have different magnetic forces.

In one embodiment, when the charger receiving unit is rotated about the hinge by pressing a bottom of the aerosol generation device while the charger receiving unit is positioned in the first position, one of the first magnetic body and the second magnetic body is distanced from the third magnetic body, and the other one of the first magnetic body and the second magnetic body comes close to the fourth magnetic body, thereby moving the charger receiving unit to the second position.

In one embodiment, when the aerosol generation device is separated from the charger receiving unit while the charger receiving unit is in the second position, the charger receiving unit returns to the first position due to an attraction force between one of the first magnetic body and the second magnetic body and the third magnetic body.

In one embodiment, the aerosol generation device may further include a cartridge opening for receiving a cigarette, and when the charger receiving unit is in the first position, the cartridge opening of the aerosol generation device provided in the charger receiving unit is not exposed to the outside, and when the charger receiving unit is in the second position, the cartridge opening of the aerosol generation device provided in the charger receiving unit is exposed to the outside.

In one embodiment, the aerosol generation device may further include a first button portion to: transmit an activation signal to the controller by means of a user's manipulation to allow the supply of electric power from the power storage unit to the heater, and transmit a deactivation signal to the controller by means of a user's manipulation during the electric power supply from the power storage unit to the heater to block the supply of electric power from the power storage unit to the heater.

In one embodiment, further provided is a second button portion to: transmit an activation signal to the auxiliary power supplying device by means of a user's manipulation to allow the supply of electric power from the auxiliary power storage device to the aerosol generation device; and transmit a deactivation signal to the auxiliary power supplying device by means of the user's manipulation during electric power supply from the auxiliary power storage device to the aerosol generation device to block the supply of electric power from the auxiliary power storage device to the aerosol generation device.

In one embodiment, the aerosol generation device may be mounted on the charger receiving unit, and when the charger receiving unit is in the first position, the aerosol generation device is driven in the charging mode.

In one embodiment, when the aerosol generation device is driven in the charging mode, electric power stored in the auxiliary power storage device of the external power supply device is delivered to the power storage unit of the aerosol generation device.

In one embodiment, when the aerosol generation device is mounted on the charger receiving unit, and the user manipulates the second button portion while the charger receiving unit is in the first position, the aerosol generation device may be driven in the cleaning mode.

In one embodiment, when the aerosol generation device is driven in the cleaning mode, the auxiliary power supplying device transmits an activation signal to the controller of the aerosol generation device to operate the heater.

In one embodiment, when the aerosol generation device is mounted on the charger receiving unit while the charger receiving unit is in the second position, the aerosol generation device may be driven in one of the preheating mode and the smoking mode.

In one embodiment, when the aerosol generation device is mounted on the charger receiving unit, and the user manipulates the second button portion while the charger receiving unit is in the second position, the aerosol generation device may be driven in the preheating mode.

In one embodiment, when the aerosol generation device is driven in the preheating mode, the auxiliary power supplying device may transmit an activation signal to the controller of the aerosol generation device to raise the temperature of the heater to an operating temperature.

In one embodiment, when the temperature of the heater is raised to the operating temperature, the aerosol generation device may be driven in the smoking mode in which the temperature of the heater is maintained at the operating temperature.

In one embodiment, the external power supply device may further include an external electric power port for connection to an external power source for the supply of electric power to the auxiliary power storage device.

In one embodiment, the charger receiving unit may include a switching member protruding in a direction facing the auxiliary power supplying device, the auxiliary power supplying device may include a third button portion which is pressed by the switching member when the charger receiving unit is in the second position, and when the third button portion is pressed, the auxiliary power supplying device transmits an activation signal to the controller of the aerosol generation device to allow the supply of electric power from the power storage unit to the heater, thereby operating the heater.

With respect to the terms in the various exemplary embodiments of the present disclosure, the general terms which are currently and widely used are selected in consideration of functions of structural elements in the various exemplary embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various exemplary embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, exemplary embodiments of the present disclosure will be described in detail with reference to the accompanying drawings. The disclosure may, however, be embodied in many different forms and should not be construed as limited to the exemplary embodiments set forth herein.

Hereinafter, exemplary embodiments of the present disclosure will be described in detail with reference to the drawings.

FIG. 1 is a schematic view illustrating an exemplary embodiment in which a cigarette is inserted into an aerosol generation device 10000.

Referring to FIG. 1, the aerosol generation device 10000 includes a battery 11000, a controller 12000, and a heater 13000. In addition, a cigarette 20000 may be inserted into the internal space of the aerosol generation device 10000.

The aerosol generation device 10000 illustrated in FIG. 1 includes only elements related to the present embodiment. Accordingly, a person skilled in the art related to the present exemplary embodiment would understand that other general use elements may be further included in the aerosol generation device 10000 in addition to the elements illustrated in FIG. 1.

FIG. 1 illustrates that the battery 11000, the controller 12000, and the heater 13000 are arranged in a line, but the arrangement is not limited thereto. In other words, according to the design of the aerosol generation device 10000, the arrangement of the battery 11000, the controller 12000, and the heater 13000 may be changed.

When the cigarette 20000 is inserted into the aerosol generation device 10000, the aerosol generation device 10000 heats the heater 13000. An aerosol-generating material in the cigarette 20000 is heated by the heater 13000, resulting in the formation of aerosol. The generated aerosol is delivered to the user through a filter 22000 of the cigarette 20000.

As necessary, even when the cigarette 20000 is not inserted into the aerosol generation device 10000, the aerosol generation device 10000 may heat the heater 13000.

The battery 11000 supplies power used to operate the aerosol generation device 10000. For example, the battery 11000 may supply power for heating the heater 13000 and may supply power for operating the controller 12000. Furthermore, the battery 11000 may supply power for operating a display, a sensor, or a motor installed in the aerosol generation device 10000.

The controller 12000 controls the operation of the aerosol generation device 10000. In detail, the controller 12000 controls operations of other components included in the aerosol generation device 100, in addition to the battery 11000 and the heater 13000. The controller 12000 may identify the state of each element of the aerosol generation device 10000 to determine whether the aerosol generation device 10000 is in an operable state.

The controller 12000 includes at least one processor. A processor may be implemented as an array of a plurality of logic gates or may be implemented as a combination of a general-purpose microprocessor and a memory in which a program executable in the microprocessor is stored. It will be understood by one of ordinary skill in the art that the present disclosure may be implemented in other forms of hardware.

The heater 13000 may be heated by the power supplied from the battery 11000. For example, when the cigarette is inserted into the aerosol generation device 10000, the heater 13000 may be located inside the cigarette. Thus, when heated, the heater 13000 may raise the temperature of an aerosol-generating material in the cigarette.

The heater 13000 may include an electrically resistive heater. For example, the heater 13000 may include an electrically conductive track, and as the current flows in the electrically conductive track, the heater 13000 may be heated. However, the heater 13000 is not limited to the above-described example, and any other example thereof may be applied without limitation as long as it is able to be heated to a target temperature. Here, the target temperature may be set in the aerosol generation device 10000 in advance or may be set to a desired temperature by the user.

Meanwhile, as another example, the heater 13000 may be an induction-heating heater. In detail, the heater 13000 may include an electrically conductive coil for heating the cigarette in an induction-heating method, and the cigarette may include a susceptor that may be heated by an induction heating heater.

FIG. 1 illustrates that the heater 13000 is inserted into the cigarette 20000, but the position of the heater 13000 is not limited thereto. For example, the heater 13000 may include a tubular heating element, a plate-type heating element, a needle-type heating element, or a rod-type heating element, and may heat the inside or the outside of the cigarette 20000 according to the shape of a heating element.

In addition, a plurality of heaters 13000 may be positioned in the aerosol generation device 10000. In this case, the plurality of heaters 13000 may be inserted into the cigarette 20000 or may be positioned outside the cigarette 20000. Otherwise, some of the plurality of heaters 13000 may be inserted into the cigarette 20000, and others may be positioned outside the cigarette 20000. In addition, the shape of the heater 13000 is not limited to the shape illustrated in FIG. 1 and may vary.

The aerosol generation device 10000 may further include general components in addition to the battery 11000, the controller 12000, and the heater 13000. For example, the aerosol generation device 10000 may include a display capable of outputting visual information and/or a motor for outputting tactile information. In addition, the aerosol generation device 10000 may include at least one sensor (a puff sensor, a temperature sensor, a cigarette insertion sensor, etc.).

In addition, the aerosol generation device 10000 may be manufactured to have a structure in which external air may be introduced or internal gas may flow out even while the cigarette 20000 is inserted.

Although not illustrated in FIG. 1, the aerosol generation device 10000 may be teamed up with a separate cradle to form a system. For example, a cradle may be used for charging the battery 11000 of the aerosol generation device 10000. In some exemplary embodiments, the heater 13000 may be heated while the cradle and the aerosol generation device 10000 are coupled.

The cigarette 20000 may be similar to a general combustion-type cigarette. For example, the cigarette 20000 may be divided into a first portion 21000 including an aerosol-generating material and a second portion 22000 including a filter or the like. In some exemplary embodiments, the second portion 22000 of the cigarette 20000 may also include an aerosol-generating material. For example, an aerosol-generating material made in the form of granules or capsules may be inserted into the second portion 22000.

The first portion 21000 may be completely inserted into the aerosol generation device 10000, and the second portion 22000 may be exposed to the outside. In some exemplary embodiments, only a portion of the first portion 21000 may be inserted into the aerosol generation device 10000, or the first portion 21000 and a portion of the second portion 22000 may be inserted thereinto. The user may puff aerosol while holding the second portion 22000 by the mouth of the user. In this case, the aerosol is generated by the external air passing through the first portion 21000, and the generated aerosol passes through the second portion 22000 and is delivered to the user's mouth.

As an example, the external air may be introduced through at least one air path formed in the aerosol generation device 10000. For example, the opening and closing of the air path formed in the aerosol generation device 10000 and/or the size of the air path may be controlled by a user. Accordingly, the amount of smoke and a smoking impression may be adjusted by the user. As another example, external air may be introduced into the cigarette 20000 through at least one hole formed in the surface of the cigarette 20000.

Hereinafter, an example of the cigarette 20000 will be described with reference to FIG. 2.

Figure 2:
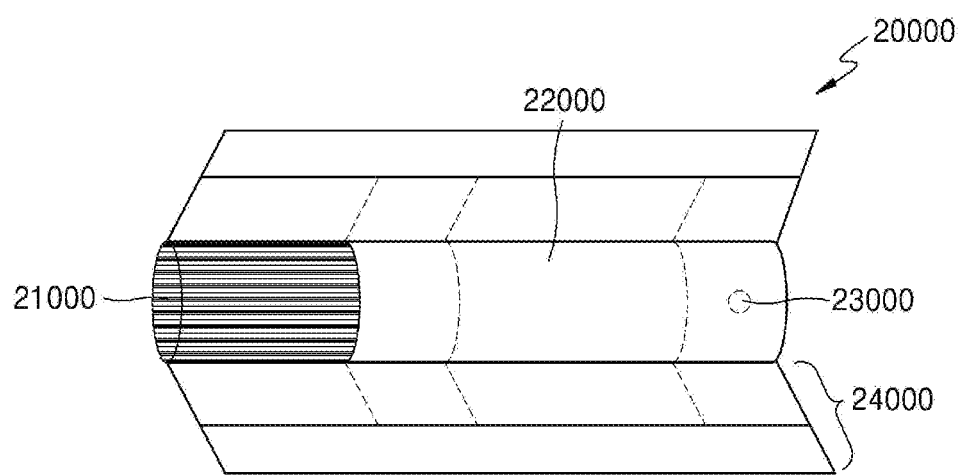
FIG. 2 shows a schematic view showing an example of a cigarette.

FIG. 2 shows an example of the cigarette 2000.

Referring to FIG. 2, the cigarette 20000 includes a cigarette rod 21000 and a filter rod 22000. The first portion 21000 described above with reference to FIG. 1 includes a cigarette rod 21000, and the second portion 32000 includes a filter rod 22000.

The filter rod 22000 of FIG. 2 is illustrated as a single segment, but is not limited thereto. In other words, the filter rod 22000 may include a plurality of segments. For example, the filter rod 22000 may include a first segment for cooling the aerosol and a second segment for filtering a certain component provided in the aerosol. In addition, if needed, the filter rod 22000 may further include at least one segment for performing another function.

The cigarette 20000 may be packaged by at least one wrapper 24000. The wrapper 24000 may have at least one hole through which external air is introduced or internal gas is discharged. As an example, the cigarette 20000 may be packaged by one wrapper 24000. As another example, the cigarette 20000 may be packaged by two or more wrappers 24000, which overlap each other. For example, the cigarette rod 21000 may be packaged by the first wrapper, and the filter rod 22000 may be packaged by the second wrapper. In addition, the cigarette rod 21000 and the filter rod 22000, which are each packaged by a separate wrapper, may be coupled, and the cigarette 20000 may be completely repackaged by a third wrapper. When each of the cigarette rod 21000 and the filter rod 22000 includes a plurality of segments, each segment may be packaged by a separate wrapper. Then, the cigarette 20000, in which the segments packaged by the separate wrappers are coupled, may be entirely repackaged by another wrapper.

The cigarette rod 21000 may include an aerosol-generating material. For example, the aerosol-generating material may include at least one of glycerin, propylene glycol, ethylene glycol, dipropylene glycol, diethylene glycol, triethylene glycol, tetraethylene glycol, and oleyl alcohol, but is not limited thereto. In addition, the cigarette rod 21000 may contain other additives such as flavors, wetting agents, and/or organic acids. In addition, a fragrance liquid such as menthol or a moisturizer may be added to the cigarette rod 21000 by being sprayed onto the cigarette rod 21000.

The cigarette rod 21000 may be manufactured in various ways. For example, the cigarette rod 21000 may be manufactured with a sheet or a strand. In addition, the cigarette rod 21000 may be manufactured with pipe tobacco blends obtained by cutting the tobacco sheet in small sizes. In addition, the cigarette rod 21000 may be surrounded by a heat conducting material. For example, the heat conducting material may be, but is not limited to, a metal foil such as aluminum foil. For example, the heat conducting material surrounding the cigarette rod 21000 may evenly distribute the heat transferred to the cigarette rod 21000 to improve the thermal conductivity applied to the cigarette rod 21000, thereby improving the taste of the cigarette. In addition, the heat conducting material surrounding the cigarette rod 21000 may function as a susceptor heated by an induction-heating heater. In this case, although not illustrated in the drawing, the cigarette rod 21000 may further include an additional susceptor in addition to the heat conducting material surrounding the outside thereof.

The filter rod 22000 may be a cellulose acetate filter. The shape of the filter rod 22000 is not limited. For example, the filter rod 22000 may be a cylindrical type rod, or may be a tube type rod having a hollow therein. In addition, the filter rod 22000 may be a recess-type rod. When the filter rod 22000 includes a plurality of segments, at least one of the segments may be manufactured in a different shape.

The filter rod 22000 may generate flavor. As one example, a fragrance liquid may be sprayed into the filter rod 22000, or a separate fiber coated with a fragrance liquid may be inserted into the filter rod 22000.

In addition, the filter rod 22000 may be provided with at least one capsule 23000. Herein, the capsule 23000 may perform the function of generating a flavor, or may perform the function of generating aerosol. For example, the capsule 23000 may have the structure of fragrance-containing liquid packaged with a coating film. The capsule 23000 may have a spherical or cylindrical shape, but the shape thereof is not limited thereto.

When the filter rod 22000 includes a segment for cooling the aerosol, the cooling segment may include a polymer material or a biodegradable polymer material. For example, the cooling segment may include pure polylactic acid alone, but the material for forming the cooling segment is not limited thereto. In some exemplary embodiments, the cooling segment may include a cellulose acetate filter having a plurality of holes. However, the cooling segment is not limited to the above-described example, and is not limited as long as the cooling segment cools the aerosol.

Figure 3:
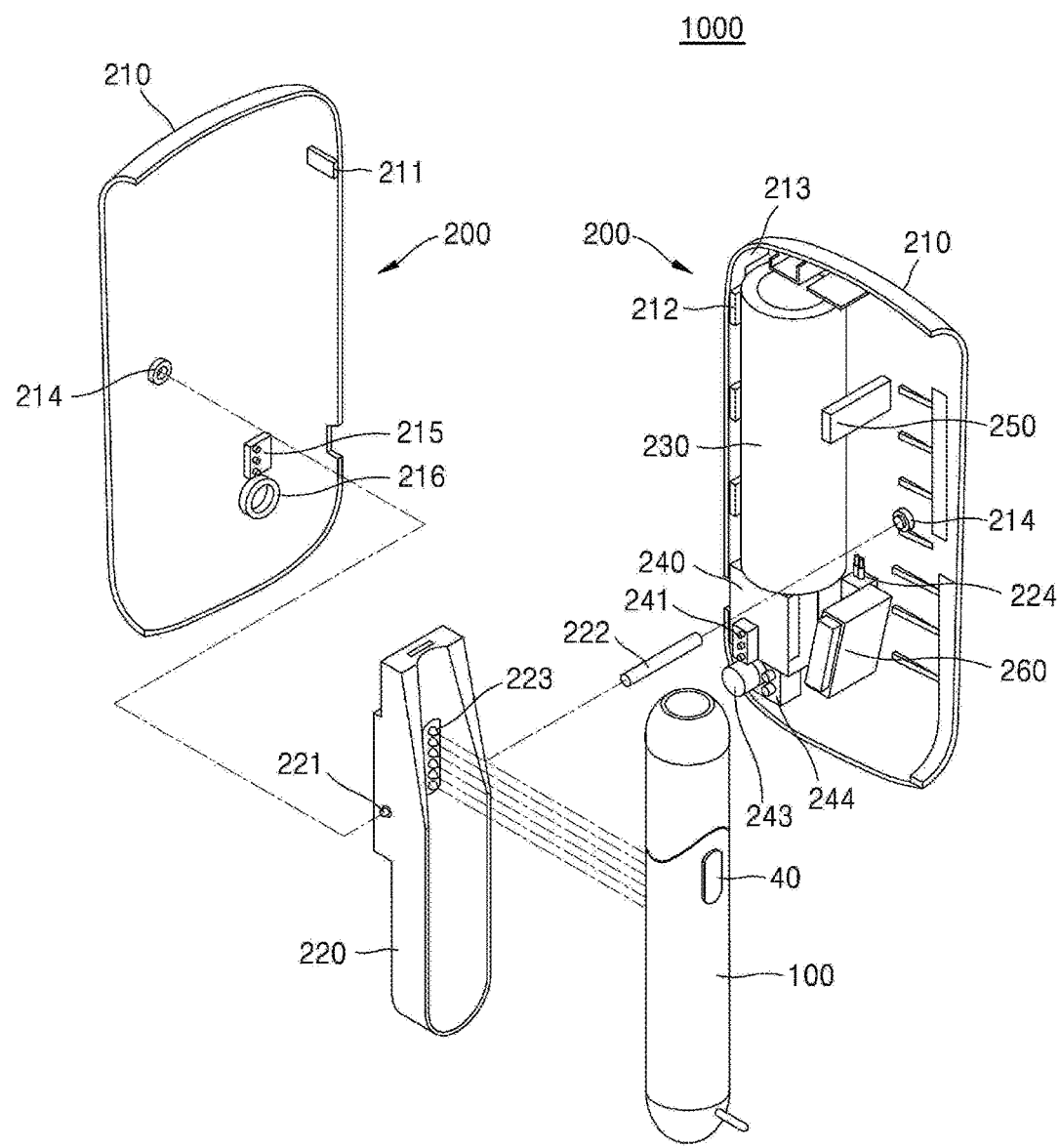
FIG. 3 shows an exploded perspective view of a charging system for an aerosol generation device according to an exemplary embodiment of the present disclosure.
Figure 4:
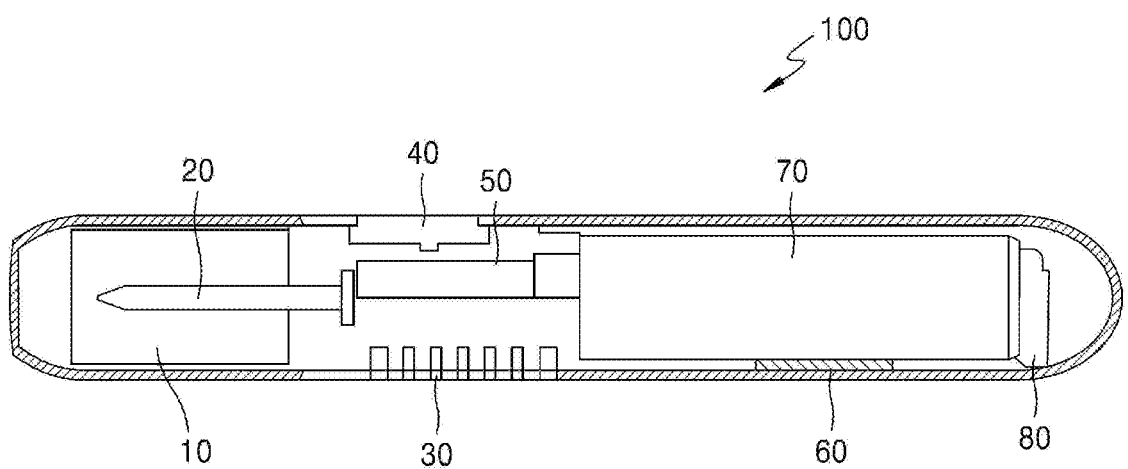
FIG. 4 shows a cross-sectional view of the aerosol generation device illustrated in FIG. 3.
Figure 5:
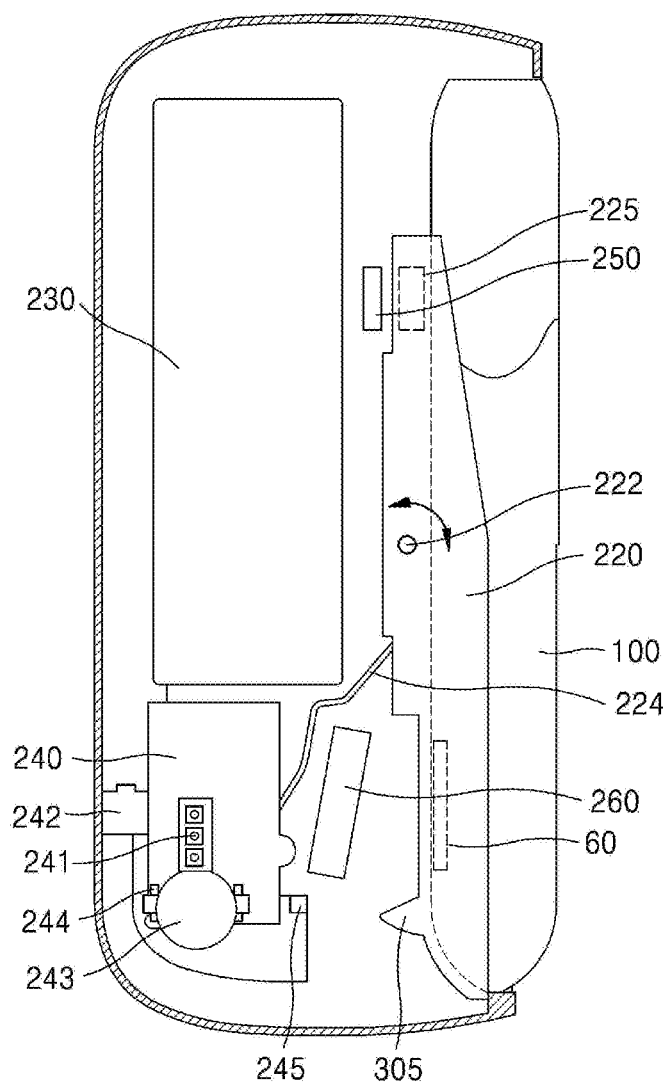
FIG. 5 shows a conceptual view illustrating a first operation example of the charging system illustrated in FIG. 3.
Figure 6:
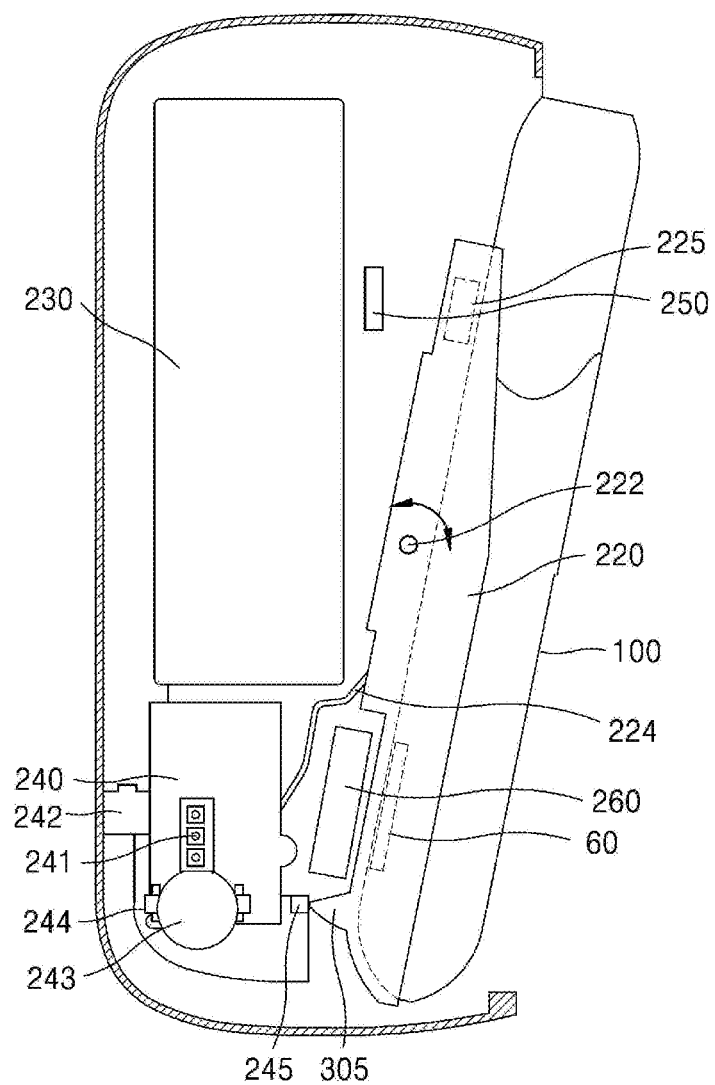
FIG. 6 shows a conceptual view illustrating a second operation example of the charging system illustrated in FIG. 3.
Figure 7:
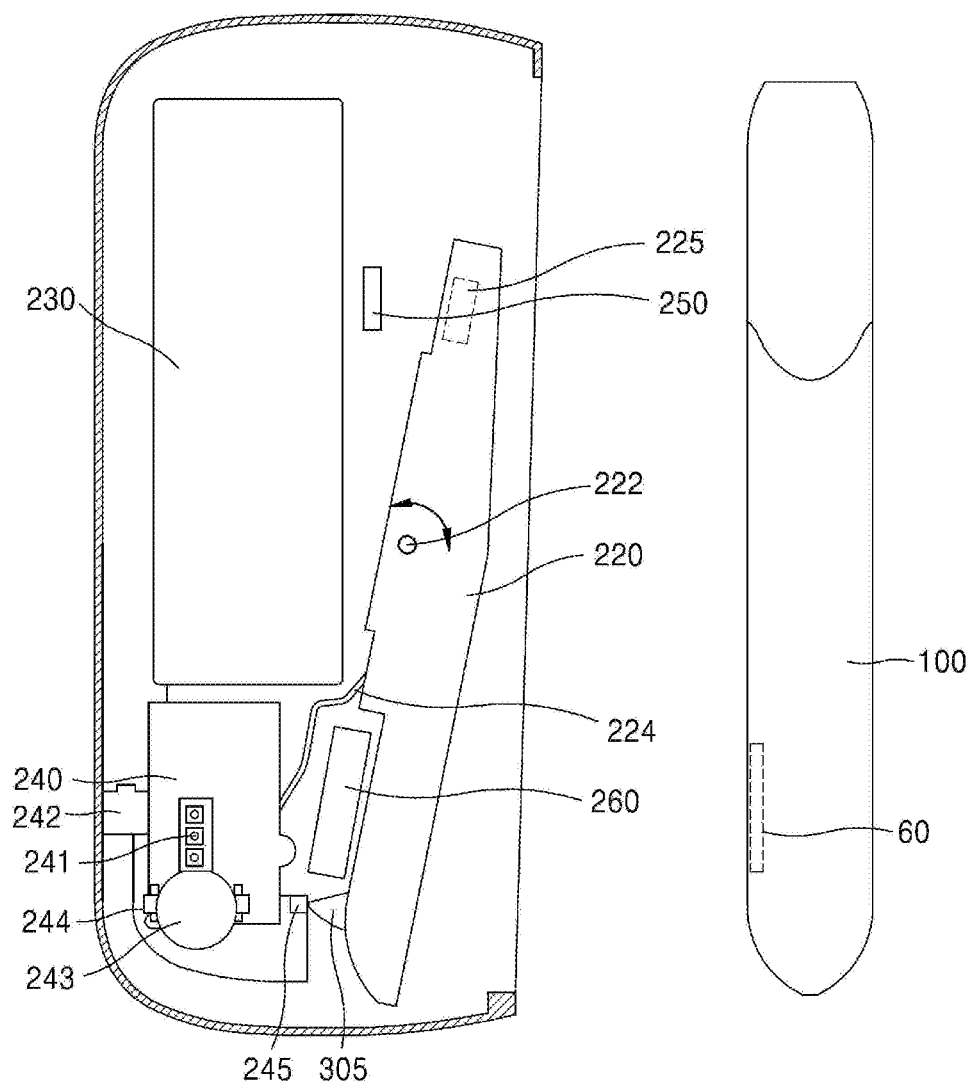
FIG. 7 shows a conceptual view illustrating a third operation example of the charging system illustrated in FIG. 3.

FIG. 3 shows an exploded perspective view of a charging system for an aerosol generation device according to an exemplary embodiment of the present disclosure. FIG. 4 shows a cross-sectional view of the aerosol generation device illustrated in FIG. 3. FIG. 5 shows a conceptual view illustrating a first operation example of the charging system illustrated in FIG. 3. FIG. 6 shows a conceptual view illustrating a second operation example of the charging system illustrated in FIG. 3. FIG. 7 shows a conceptual view illustrating a third operation example of the charging system illustrated in FIG. 3.

Referring to FIGS. 3 to 5, a charging system for an aerosol generation device (hereinafter, "charging system") 1000 includes an aerosol generation device 100 and an external power supply device 200. The aerosol generation device 100 may include a heater 20 for generating heat by resistance when a current is applied thereto, a power storage unit 70 for supplying electric power to the heater 20, and a controller 50 for controlling the heater 20. The external power supply device 200 may include a case 210, a charger receiving unit 220 which is mounted rotatably on the case 210 and receives the aerosol generation device 100 in a detachable and attachable manner, an auxiliary power storage device 230 for storing the power to be delivered to the aerosol generation device 100, and an auxiliary power supplying device 240 for controlling the auxiliary power storage device 230 which supplies electric power to the aerosol generation device 100.

Referring to FIG. 4, the aerosol generation device 100 includes a first button portion 40 which is to be pressed to preheat the aerosol generation device 100, the heater 20 which generates heat by resistance when a current is applied, the power storage unit 70 which instantaneously provides a high level of power to the heater 20, and a controller 50 for controlling the heater 20. The heater 20 generates aerosol by heating a vaporizing material contained in the cartridge 10, the vaporizing material including an aerosol-generating material which vaporizes when heated above a predetermined temperature.

For example, when the user manipulates the first button portion 40 to transmit an activation signal to the controller 50, power is supplied from the power storage unit 70 to the heater 20 and thus the heater 20 may be heated. On the contrary, when the user manipulates the first button portion 40 while the heater 20 is being heated, a deactivation signal is transmitted to the controller 50 to cut off the power supply from the power storage unit 70 to the heater 20.

When a cigarette-type electronic cigarette filled with paper which is impregnated with or coated with a puffing material is inserted into the cartridge 10, the heater 20 is heated and the puffing material inside the cigarette portion is vaporized. As a result, the user may puff the vaporized puffing material through a filter portion.

When the aerosol generation device 100 is unable to operate due to insufficient power in the heater 20, or when the aerosol generation device 100 is ready for operation, the controller 50 drives a motor 80 to produce the vibration of the aerosol generation device, leading to the recognition by the user.

In addition, the controller 50 displays the remaining electric power level of the power storage unit 70 on a first display unit (not shown) formed in the aerosol generation device 100, and even when the aerosol generation device 100 is unable to operate due to the insufficient power supplied to the heater 20, the controller 50 displays the state of the power storage unit 70 on the first display unit.

When the aerosol generation device 100 is received in the charger receiving unit 220 of the external power supply device 200, the power storage unit 70 may receive electric power via wire-connection through a second charging terminal 30 of the aerosol generation device 100 connected to a first charging terminal 223 of the charger receiving unit 220, and when the aerosol generation device 100 receives electric power, the controller 50 may display the level of electric power supplied to the external power supply device 200 on a second display unit (not shown).

In detail, the controller 50 may control the amount of electric power charged to the power storage unit 70 from the auxiliary power storage device 230 of the external power supply device 200 in such a manner that the power storage unit 70 is charged with electric power sufficient for a cigarette-type electronic cigarette received in the aerosol generation device 100 to proceed with one cycle of preheating and puffing.

In addition, the aerosol generation device 100 may perform data communication with the first charging terminal 223 of the external power supply device 200 through the second charging terminal 30. In addition, the aerosol generation device 100 may include a separate wireless communication port. The controller 50 controls a communication between a wireless communication port provided in the aerosol generation device 100 and a wireless communication port provided in the external power supply device 200, thereby enabling data communication with the auxiliary power supplying device 240 and wireless supply of electric power by the external power supply device 200.

The power storage unit 70 is separable from the aerosol generation device 100, and the external power supply device 200 includes a plurality of housing portions that are able to receive the power storage unit 70, thereby enabling receiving and charging one or more power storage units 70 separated from the aerosol generation device 100.

In addition, the aerosol generation device 100 may include a power generating unit for converting external energy such as light energy or mechanical energy into electric energy to produce electric power by itself to charge the power storage unit 70.

Referring to FIGS. 3 and 5, the external power supply device 200 has a case 210 that may be separated into parts, and, the inside of the case 210 is partitioned to allow components of the external power supply device 200 to be mounted therein. Also, a plurality of hooks 211 and fixing grooves 212 are provided to allow the case 210 to be coupled to each other.

The charger receiving unit 220 is rotatably installed in the case 210 to accommodate the aerosol generation device 100 in a detachable/attachable manner. The charger receiving unit 220 is rotatable about the case 210 by a hinge 222 which is inserted through holes 221 formed at both sides of the charger receiving unit 220 and also inserted into grooves 214 formed inside the case 210.

In detail, the charger receiving unit 220 may be rotatable between a first position (see FIG. 5) where the charger receiving unit 220 is parallel to the longitudinal direction of the case 210 and a second position where the charger receiving unit 220 tilted with respect to the longitudinal direction of the case 210 (see FIG. 6). That is, the charger receiving unit 220 may be mounted on the case 210 in such a manner that the charger receiving unit 220 is rotatable about the hinge 222 between the first position in which a cartridge opening 11 of the aerosol generation device 100 is not exposed to the outside of the external power supply device 200 and the second position in which the cartridge opening 11 of the aerosol generation device 100 is exposed to the outside of the external power supply device 200.

In addition, one side of the charger receiving unit 220 facing the aerosol generation device 100 may be formed in the same shape as the aerosol generation device 100 to stably receive the aerosol generation device 100. In addition, the auxiliary power storage device 230 and the auxiliary power supplying device 240 are connected by wiring, and the auxiliary power supplying device 240 is connected to the first charging terminal 223 formed in the charger receiving unit 220 by the wiring 224.

The auxiliary power storage device 230 stores electric power to be delivered to the aerosol generation device 100, and the auxiliary power supplying device 240 controls the auxiliary power storage device 230 to supply electric power to the aerosol generation device 100. The auxiliary power storage device 230 and the auxiliary power supplying device 240 may be mounted on a housing portion 213 of the external power supply device 200.

The auxiliary power supplying device 240 controls the auxiliary power storage device 230 to be charged via a conventional external power source built in the case, such as an external electric power port 242, and displays the charge state of the auxiliary power storage device 230 by means of an LED 241. Herein, the external electric power port 242 may include a USB port or a general electric terminal.

For example, the LED 241 may include three LEDs, and according to the amount of electric power charged, one LED or two or three LEDs may be turned on. When three LEDs are turned on, it may indicate that the auxiliary power storage device 230 is fully charged.

Each LED 241 mounted on a part of the case 201 may be exposed outside the case 201 through a hole 215 formed in the other part of the case 201. In addition, inside the case 210, provided is a second button portion 243 protruding outside the case 210 through a hole 216, and the second button portion 243 is supported by a fixing protrusion 244 inside the case 210.

The second button portion 243 is connected to the auxiliary power supplying device 240 via wiring, and when the user manipulates the second button portion 243, an activation signal may be transmitted to the auxiliary power supplying device 240 to allow electric power supply from the auxiliary power storage device 230 to the aerosol generation device 100. When the user manipulates the second button portion 243 again while the electric power is supplied from the auxiliary power storage device 230 to the aerosol generation device 100, the electric power supply from the auxiliary power storage device 230 to the aerosol generation device 100 may be cut off.

For example, as illustrated in FIG. 5, when the user presses the second button portion 243 while the aerosol generation device 100 is attached on the charger receiving unit 220 and the charger receiving unit 220 is positioned to be parallel to the longitudinal direction of the case 210, the auxiliary power supplying device 240 may operate in a cleaning mode in which an electric power is supplied from the auxiliary power storage device 230 to the aerosol generation device 100 to clean the aerosol generation device 100 by dissolving ash or debris on the aerosol generation device 100.

In detail, a signal generated when the user manipulates the second button portion 243 is transmitted, via wiring, from the auxiliary power supplying device 240 to the controller 50 of the aerosol generation device 100 through the first charging terminal 223 of the charger receiving unit 220 and the second charging terminal 30 of the aerosol generation device 100, and thus, the heater 20 of the aerosol generation device 100 is operated.

That is, although the first button portion 40 of the aerosol generation device 100 is not operated separately, the heater 20 of the aerosol generation device 100 may be operated by manipulating the second button portion 243 of the external power supply device 200 while the aerosol generation device 100 is mounted on the charger receiving unit 220 and the charger receiving unit 220 is positioned parallel to the longitudinal direction of the case 210.

In addition, even when there is no manipulation of the second button portion 243, as illustrated in FIG. 5, the aerosol generation device 100 may be driven in a charging mode while the charger receiving unit 220 is positioned in parallel to the longitudinal direction of the case 210 and the aerosol generation device 100 is attached on the charger receiving unit 220. That is, when the aerosol generation device 100 is mounted on the charger receiving unit 220 while the charger receiving unit 220 is positioned parallel to the length of the case 210, even without the user's manipulation, the auxiliary power supplying device 240 supplies electric power from the auxiliary power storage device 230 to the power storage unit 70 of the aerosol generation device 100, thereby charging the aerosol generation device 100.

Meanwhile, as illustrated in FIG. 6, when the user presses the second button portion 243 while the aerosol generation device 100 is attached on the charger receiving unit 220 and the charger receiving unit 220 is tilted with respect to the longitudinal direction of the case 210, the aerosol generation device 100 may operate in a preheating mode in which electric power is supplied from the auxiliary power storage device 230 to the aerosol generation device 100 by the auxiliary power supplying device 240 to preheat the aerosol generation device 100.

That is, while the aerosol generation device 100 is received by the charger receiving unit 220, the first charging terminal 223 of the charger receiving unit 220 is connected to the second charging terminal 30 facing the first charging terminal 223 of the aerosol generation device 100, and due to the control of the auxiliary power supplying device 240, the electric power of the auxiliary power storage device 230 is supplied to the aerosol generation device 100. The auxiliary power supplying device 240 may include a wireless communication port. Accordingly, the auxiliary power supplying device 240 may supply electric power directly to the aerosol generation device 100 in a wireless manner as well as a wired manner.

For example, when the user manipulates the second button portion 243 to transmit an activation signal to the auxiliary power supplying device 240, electric power may be supplied from the auxiliary power storage device 230 to the aerosol generation device 100 to heat the heater 20 of the aerosol generation device 100. On the contrary, when the user manipulates the second button portion 243 while the heater 20 is being heated, a deactivation signal is transmitted to the auxiliary power supplying device 240 to block the supply of electric power from the auxiliary power storage device 230 to the aerosol generation device 100.

In some exemplary embodiments, the charger receiving unit 220 includes a switching member 305 for pressing a third button portion 245 provided on the auxiliary power supplying device 240 of the external power supply device 200. When the charger receiving unit 220 rotates from the first position to the second position (from the position illustrated in FIG. 5 to the position illustrated in FIG. 6), the switching member 305 presses the third button portion 245, which causes the auxiliary power supplying device 240 to supply the electric power of the auxiliary power storage device 230 to the aerosol generation device 100 through the first charging terminal 223 of the charger receiving unit 220, even without the pressing of the second button portion 243, to preheat the aerosol generation device 100.

Meanwhile, the case 210 may be provided with a first magnetic body 250 and a second magnetic body 260, which are positioned on the opposite sides of the rotation axis of the charger receiving unit 220, that is, the hinge 222. The charger receiving unit 220 includes a third magnetic body 225 facing one of the first magnetic body 250 and the second magnetic body 260. Although the drawing illustrates that the third magnetic body 225 is positioned to face the first magnetic body 250, exemplary embodiments of the present disclosure are not limited thereto, and the third magnetic body 225 may be positioned to face the second magnetic body 260 at the bottom of the charger receiving unit 220. However, hereinafter, for ease of description, the third magnetic body 225 is assumed to be provided to face the first magnetic body 250 at the top of the charger receiving unit 220.

In addition, one of the first magnetic body 250 and the second magnetic body 260 may be provided to be inclined with respect to the longitudinal direction of the case 210 in the case 210. Although the drawing illustrates the second magnetic body 260, positioned below the external power supply device 200, inclined relative to the length of the case 210, exemplary embodiments of the present disclosure are not limited thereto, and instead, the first magnetic body 250 may be positioned to be inclined with respect to the longitudinal direction of the case 210 in the case 210. However, hereinafter, for ease of description, the exemplary embodiment in which the second magnetic body 260 is provided to be inclined with respect to the longitudinal direction of the case 210, will be described.

In addition, the aerosol generation device 100 may include a fourth magnetic body 60 facing either the first magnetic body 250 or the second magnetic body 260 that does not face the third magnetic body 225 (e.g., the second magnetic body 260 in FIG. 6).

To summarize the structure described above, the first magnetic body 250 and the second magnetic body 260 are respectively provided at the top and bottom of the case 210 of the external power supply device 200, and the third magnetic body 225 facing the first magnetic body 250 is positioned at the top of the charger receiving unit 220. The fourth magnetic body 60 facing the second magnetic body 260 is positioned at the bottom of the aerosol generation device 100.

Herein, an attraction force may be applied between the first magnetic body 250 and the third magnetic body 225, between the first magnetic body 250 and the fourth magnetic body 60, between the second magnetic body 260 and the third magnetic body 225, and between the second magnetic body 260 and the fourth magnetic body 60.

Accordingly, according to the structure as described above, when the user mounts the aerosol generation device 100 on the charger receiving unit 220 and presses the top portion of the aerosol generation device 100, due to the attraction force formed between the first magnetic body 250 and the third magnetic body 225, the first position of the charger receiving unit 220, parallel to the longitudinal direction of the case 210 as illustrated in FIG. 5, may be maintained.

While the aerosol generation device 100 is mounted on the charger receiving unit 220 as illustrated in FIG. 5, the user presses the bottom of the aerosol generation device 100 with force sufficient to overcome the attraction force formed between the first magnetic body 250 and the third magnetic body 225, as illustrated in FIG. 6, the charger receiving unit 220 rotates clockwise and ultimately, the charger receiving unit 220 is tilted with respect to the longitudinal direction of the case 210 due to the attraction force between the third magnetic body 260 and the fourth magnetic body 60.

In this case, since the second magnetic body 260 is mounted on the case 210 to be inclined with respect to the longitudinal direction of the case 210 as described above, the aerosol generation device 100 is tilted at an angle corresponding to the inclination angle of the second magnetic body 260 in the external power supply device 200.

Thereafter, the user may separate the aerosol generation device 100 from the external power supply device 200 by applying force enough to overcome the attraction force between the second magnetic body 260 and the fourth magnetic body 60 to the tilted aerosol generation device 100, as illustrated in FIG. 7.

On the other hand, the fourth magnetic body 60 may be formed to have a round cross-section, and the power storage unit 70 installed in the aerosol generation device 100 may have a cylindrical shape so that the fourth magnetic body 60 partially surrounds the outer portion of the power storage unit 70. In addition, the second charging terminal 30 may be provided at an extension line of the centerline of the fourth magnetic body 60 in the aerosol generation device 100. The aerosol generation device 100 is connected to the external power supply device 200 through the interface of the second charging terminal 30. Under control of the controller 50, while a cigarette (not shown) including a puffing material which is vaporized by heating is received, the electric power may be supplied from the auxiliary power storage device 230 of the external power supply device 200 to the heater 20 via the second charging terminal 30, during a preheating mode in which the temperature of the puffing material is raised to an operating temperature and a smoking mode in which the temperature of the puffing material is maintained substantially at the operating temperature.

Figure 8:
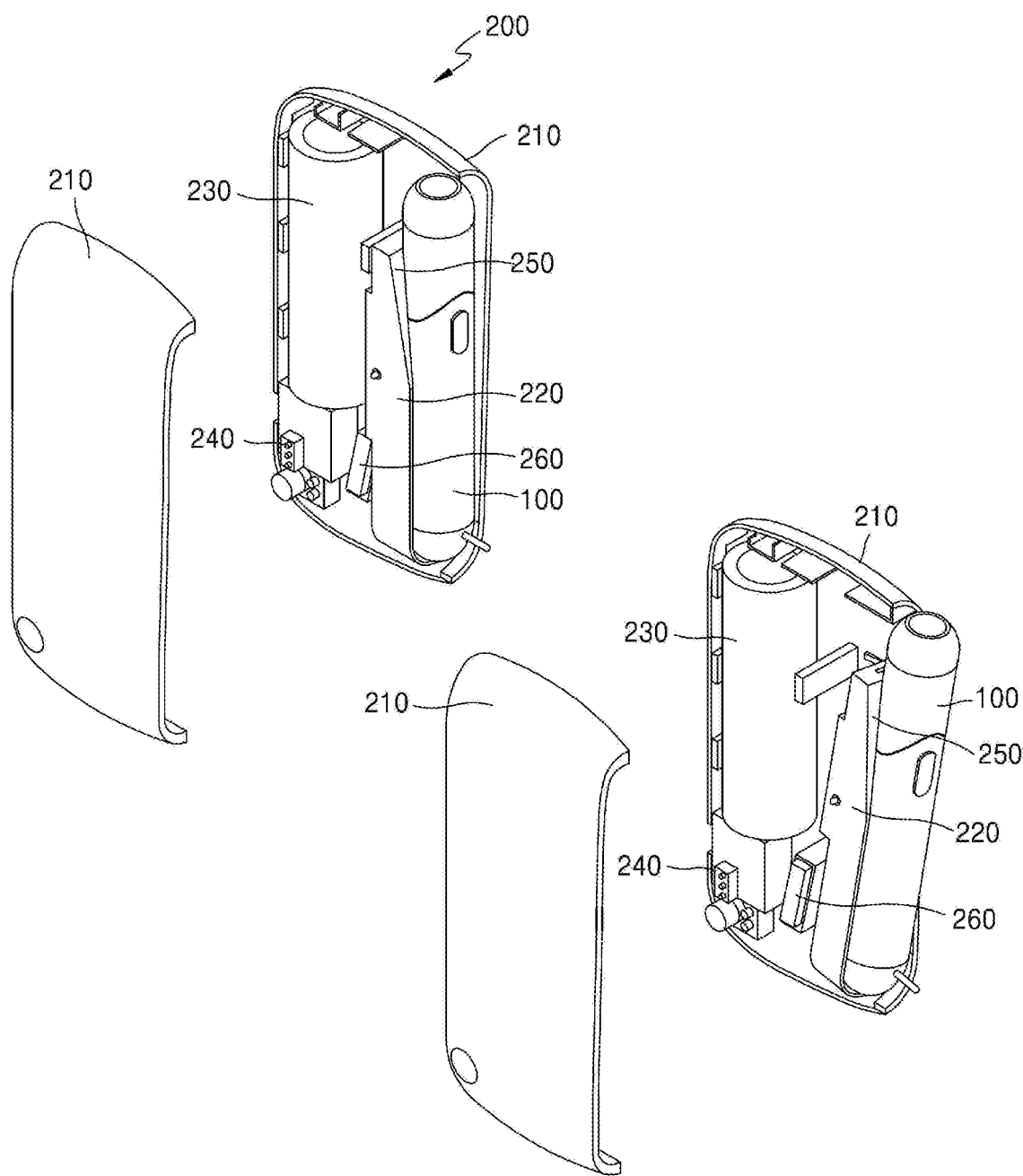
FIG. 8 shows an exploded perspective view illustrating a state in which the aerosol generation device illustrated in FIG. 3 is usable while accommodated in an external power supply device.

FIG. 8 shows an exploded perspective view illustrating a state in which the aerosol generation device 100 illustrated in FIG. 3 is operable while received in an external power supply device.

Referring to FIG. 8, the aerosol generation device 100 may be received in the charger receiving unit 220 of the external power supply device 200 and receive electric power. In order to use the aerosol generation device 100, the user may press the bottom portion of the aerosol generation device 100 while the aerosol generation device 100 is received due to the fourth magnetic body 60 in the charger receiving unit 220 of the external power supply device 200. Then, the charger receiving unit 220 may come close to the second magnetic body 260 of the case 210 which is inclined at a certain angle, while the aerosol generation device 100 is received in the charger receiving unit 220 due to the fourth magnetic body 60 of the aerosol generation device 100.

Accordingly, the upper portion of the aerosol generation device 100 is tilted and drawn to the outside, and the user may insert a cigarette to the cartridge 10 of the aerosol generation device 100 protruding to the outside and press the second button portion 243 of the external power supply device 200 to preheat the aerosol generation device 100.

Thus, the aerosol generation device 100 may be used continuously without interrupting the puffing and receive electric power from the external power supply device 200.

Figure 9:
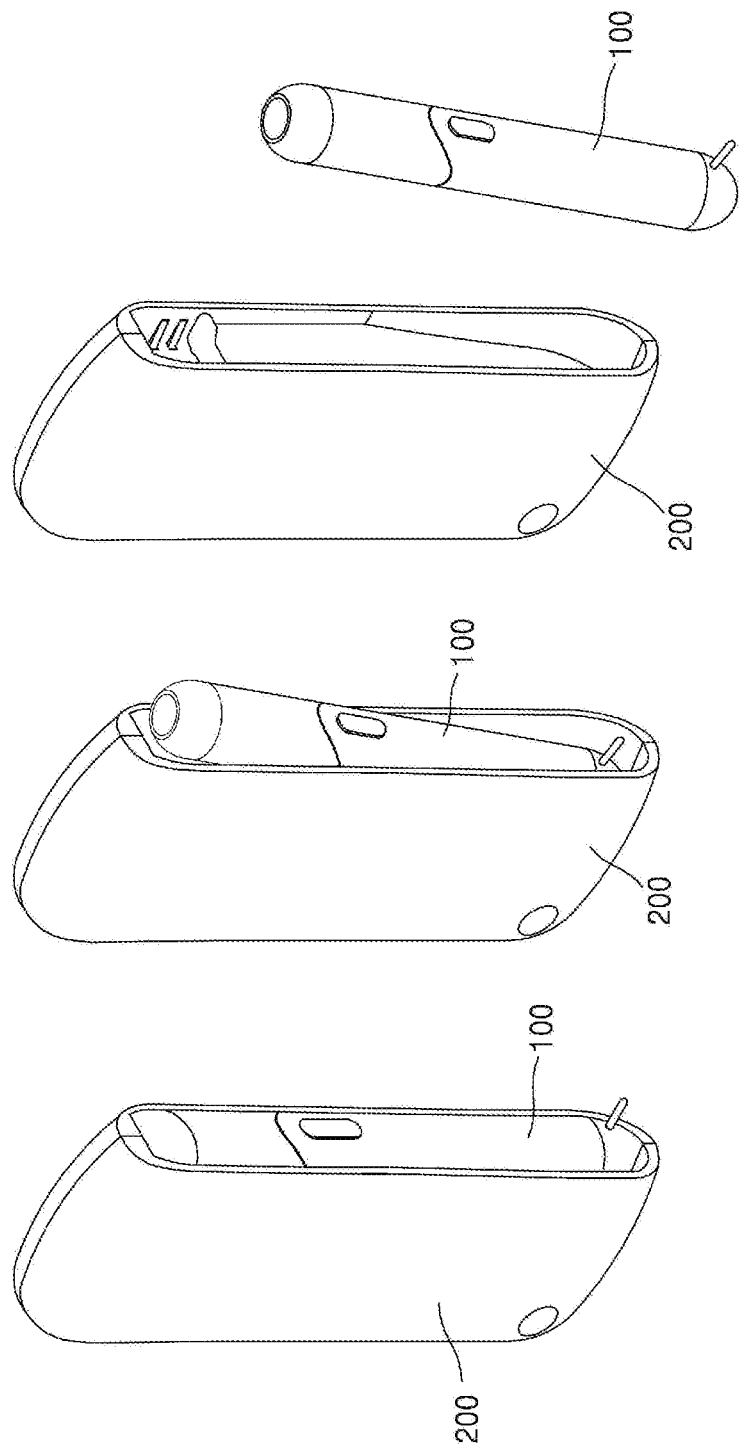
FIG. 9 shows a perspective view illustrating a process in which the aerosol generation device illustrated in FIG. 3 is separated from an external power supply device.

FIG. 9 shows a perspective view illustrating a process in which the aerosol generation device 100 illustrated in FIG. 3 is separated from the external power supply device 200.

Referring to FIG. 9, in order to separate the aerosol generation device 100 from the external power supply device 200, as described above, the user may apply a certain strength of force to the aerosol generation device 100 while the aerosol generation device 100 is tilted with respect to the external power supply device 200 and thus a portion of the aerosol generation device 100 protrudes. By doing so, the magnetic force between the aerosol generation device 100 and the external power supply device 200 is overcome and the aerosol generation device 100 is drawn out.

Figure 10:
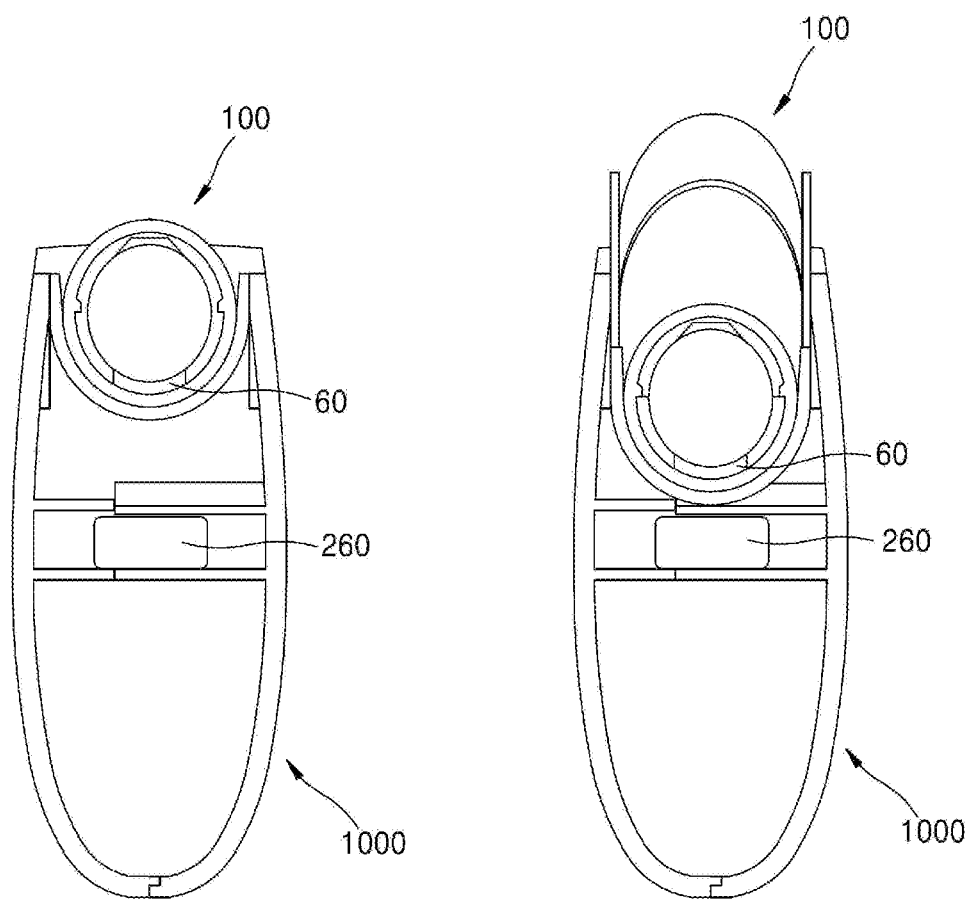
FIG. 10 shows the bottom view of the aerosol generation device of FIG. 3 to describe the arrangement of the aerosol generation device in a first position and a second position inside the charger receiving unit.

FIG. 10 illustrates the bottom view of the aerosol generation device 100 of FIG. 3 to describe the arrangement of the aerosol generation device 100 in the first position and the second position inside the charger receiving unit 220.

Referring to FIG. 10, as described above, since the fourth magnetic body 60 has a round cross-section in the aerosol generation device 100. As such, when the aerosol generation device 100 is received in the charger receiving unit 220 in the first position and the second position and the aerosol generation device 100 is misaligned from the centerline of the fourth magnetic body 60 in the charger receiving unit 220, since the strength of the magnetic force is highest at the shortest distance between a magnetic body and the centerline of the magnetic body, the aerosol generation device 100 may be aligned in the charger receiving unit 220 in such a manner that the distance between the centerline of the fourth magnetic body 60 and the second magnetic body 260 becomes the shortest, and thus, the first charging terminal 223 of the charger receiving unit 220 and the second charging terminal 30 of the aerosol generation device 100 electrically contact each other.

As described above, the present disclosure has been described with reference to exemplary embodiments shown in the drawings, which are examples only, and it will be understood by those skilled in the art that various modifications and exemplary embodiments may be made therefrom. Therefore, the true technical protection scope of the present disclosure will be defined by the technical spirit of the attached claims.

According to the exemplary embodiments described above, a charging system for an aerosol generation device that is capable of vaporizing an aerosol generation material without combustion may be provided.

What is claimed is:

1. A system for charging an aerosol generation device, the system comprising:
    an aerosol generation device comprising a heater for generating heat by resistance when a current is applied to the heater, a power storage unit for supplying electric power to the heater, and a controller for controlling the heater; and
    an external power supply device comprising a case, a charger receiving unit mounted rotatably on the case and configured to receive the aerosol generation device in a detachable and attachable manner, an auxiliary power storage device for storing electric power to be delivered to the aerosol generation device, and an auxiliary power supplying device for controlling the auxiliary power storage device to supply the electric power to the aerosol generation device, wherein the aerosol generation device is driven in one mode from among a charging mode, a cleaning mode, a preheating mode, and a smoking mode, according to where the aerosol generation device is received in the charger receiving unit, wherein the charger receiving unit is rotatable between a first position where the charger receiving unit is positioned parallel to a longitudinal direction of the case and a second position where the charger receiving unit is tilted with respect to the longitudinal direction of the case, wherein the external power supply device further comprises a first magnetic body and a second magnetic body provided on the case, the first magnetic body and the second magnetic body being positioned on opposite sides of a rotation axis of the charger receiving unit, and wherein the charger receiving unit comprises a third magnetic body facing one of the first magnetic body and the second magnetic body.

2. The system of claim 1, wherein
a hole is formed to penetrate the charger receiving unit,
grooves corresponding to the hole is formed inside the case,
the charger receiving unit is coupled to the case by means of a hinge inserted into the hole and the grooves, and
the charger receiving unit is rotatable about the hinge with respect to the case.

3. The system of claim 1, wherein
the charger receiving unit comprises a first charging terminal which is exposed to outside and electrically connected to the auxiliary power storage device and the auxiliary power supplying device, and
the aerosol generation device further comprises a second charging terminal that is connected to the first charging terminal when the aerosol generation device is inserted in the charger receiving unit such that electric power is supplied from the auxiliary power storage device to the aerosol generation device through the first charging terminal.

4. The system of claim 1, wherein
the charger receiving unit further comprises a fourth magnetic body facing the other one of the first magnetic body and the second magnetic body.

5. The system of claim 4, wherein
the charger receiving unit maintains the first position by attraction force between the third magnetic body and one of the first magnetic body and the second magnetic body, and maintains the second position by an attraction force between the fourth magnetic body and the other one of the first magnetic body and the second magnetic body.

6. The system of claim 4, wherein
when the aerosol generation device is received in the charger receiving unit, the charger receiving unit aligns the aerosol generation device inside the charger receiving unit in such a manner that a distance between a centerline of the fourth magnetic body and the other one of the first magnetic body and the second magnetic body is minimized.

7. The system of claim 1, wherein
the aerosol generation device further comprises a first button portion configured to receive a user's manipulation input to block or allow supply of the electric power from the power storage unit to the heater.

8. The system of claim 1, wherein
the external power supply device further comprises a second button portion configured to receive a user's manipulation input to block or allow supply of the electric power from the auxiliary power storage device to the aerosol generation device.

9. The system of claim 7, wherein
when the charger receiving unit, in which the aerosol generation device is received, is in the first position where the charger receiving unit is positioned parallel to a longitudinal direction of the case, the aerosol generation device is driven in the charging mode, and
when the aerosol generation device is driven in the charging mode, the electric power stored in the auxiliary power storage device is delivered to the power storage unit of the aerosol generation device.

10. The system of claim 8, wherein
when the second button portion is manipulated while the charger receiving unit, in which the aerosol generation device is received, is in the first position where the charger receiving unit is positioned parallel to a longitudinal direction of the case, the aerosol generation device is driven in the cleaning mode, and
when the aerosol generation device is driven in the cleaning mode, the auxiliary power storage device activates the heater of the aerosol generation device.

11. The system of claim 8, wherein
when the charger receiving unit, in which the aerosol generation device is received, is in the second position where the charger receiving unit is tilted with respect to a longitudinal direction of the case, the aerosol generation device is driven in one of the preheating mode and the smoking mode.

12. The system of claim 11, wherein
when the second button portion is manipulated while the charger receiving unit, in which the aerosol generation device is received, is in the second position, the aerosol generation device is driven in the preheating mode, and
when the aerosol generation device is driven in the preheating mode, the auxiliary power supplying device raises a temperature of the heater to an operating temperature.

13. The system of claim 12, wherein,
when the temperature of the heater is raised to the operating temperature, the aerosol generation device is driven in the smoking mode in which the temperature of the heater is maintained at the operating temperature.

14. The system of claim 1, wherein
the charger receiving unit comprises a switching member protruding toward the auxiliary power supplying device,
the auxiliary power supplying device comprises a third button portion configured to be pressed by the switching member when the charger receiving unit is in the second position, and
when the third button portion is pressed, the auxiliary power supplying device supplies the electric power from the power storage unit to the heater of the aerosol generation device, thereby operating the heater.

* * * * *